(12) United States Patent
Parizek et al.

(10) Patent No.: US 6,743,430 B1
(45) Date of Patent: Jun. 1, 2004

(54) MULTICOMPONENT VACCINE CONTAINING CLOSTRIDIAL AND NON-CLOSTRIDIAL ORGANISMS IN A LOW DOSE

(76) Inventors: Richard E. Parizek, Bayer Corporation, 100 Bayer Rd., Pittsburgh, PA (US) 15205-9741; Lonny E. Vlieger, Bayer Corporation, 100 Bayer Rd., Pittsburgh, PA (US) 15205-9741; Sharon A. Bryant, Bayer Corporation, 100 Bayer Rd., Pittsburgh, PA (US) 15205-9741; Stuart K. Nibbelink, Bayer Corporation, 100 Bayer Rd., Pittsburgh, PA (US) 15205-9741; Michael J. McGinley, Bayer Corporation, 100 Bayer Rd., Pittsburgh, PA (US) 15205-9741

( * ) Notice: Subject to any disclaimer, the term of this patent is extended or adjusted under 35 U.S.C. 154(b) by 0 days.

(21) Appl. No.: 08/412,676

(22) Filed: Mar. 29, 1995

(51) Int. Cl.[7] ............... A01N 63/00; A61K 39/395; A61K 39/116; A61K 39/295
(52) U.S. Cl. ............... 424/203.1; 424/93.3; 424/93.41; 424/130.1; 424/156.1; 424/163.1; 424/167.1; 424/184.1; 424/201.1; 424/239.1; 424/247.1; 424/255.1; 424/282.1
(58) Field of Search ............... 424/93.3, 93.41, 424/201.1, 203.1, 239.1, 247.1, 255.1, 256.1, 282.1, 93.4, 130.1, 156.1, 163.1, 167.1, 184.1

(56) References Cited

U.S. PATENT DOCUMENTS

| 3,920,811 A | * 11/1975 | Lund ............... 424/88 |
| 3,925,544 A | 12/1975 | Shechmeister et al. ....... 424/89 |
| 4,292,307 A | 9/1981 | Zemlyakova ............... 424/92 |

FOREIGN PATENT DOCUMENTS

| GB | 2050830 | 1/1981 | |
| WO | 94-22476 | * 10/1994 | ......... A61K/39/08 |

OTHER PUBLICATIONS

Vision Vaccines. 1992. Press release: pp. 1–11.*
Bahasefat et al Arch. Inst Razi 28:51–56 (Translation of French Article), 1976.*
Seifert et al Deutsche Tier Avztilche Wochenschrift 7: 274–279 Translation of Germ, 1983.*
Green et al Veterinary Record 120:435–439, 1987.*
Animal Pharm vol. 203 p. 28, May 20, 1996.*
Animal Pharm. vol. 124 p. 19, 1987 (Hoechst).*
Animal Pharm 292 p. 12 Jan. 14, 1994 (2).*
Webster et al Aust Vet. Journal 62:112–114 1985.*
Compenidum of Veterinary Products, Third Edition, (month unavailable) 1995–1996, pp. 133, 191, 192, 319, 320, 321, 322, 432, 433, 490, 1013, 1183, 1184 and 1185.
Stokka et al J. Am. Vet Med. Assoc., Feb. 1, 1994, vol. 204, No. 3, 415–419.
Effertz, Beef Today, Mar. 1991.
Beef Today, Sep. 1992.
Dittmer, CALF News Cattle Feeder, Sep. 1992.
Smith, FEEDSTUFFS, Aug. 24, 1992.
Hrehocik et al , dvm, Sep. 1992.
Advertising Brochure entitled ALPHA–7TH™–JUST ONCE (Date unavailable).

* cited by examiner

Primary Examiner—Lynette R. F. Smith
Assistant Examiner—JaNa Hines
(74) Attorney, Agent, or Firm—William M. Blackstone; William P. Ramey, III

(57) ABSTRACT

Disclosed herein is a multicomponent low dose vaccine comprising a safe and immunogenically effective combination of a protective antigen component or components of clostridial organism, a protective antigen component of a non-clostridial organism and an adjuvant.

9 Claims, No Drawings

MULTICOMPONENT VACCINE CONTAINING CLOSTRIDIAL AND NON-CLOSTRIDIAL ORGANISMS IN A LOW DOSE

BACKGROUND OF THE INVENTION

1. Field of the Invention

The present invention relates to low dose multicomponent vaccines. More specifically, the invention relates to low dose multicomponent vaccines comprising a safe and immunogenically effective combination of: at least one protective antigen component from clostridial organisms, at least one protective antigen component from a non-clostridial organism and an adjuvant.

2. Brief Description of the Prior Art

Preparation and formulation of multicomponent vaccines have historically been complicated by physical and technological hurdles. Multicomponent vaccines of interest are those vaccines that contain as essential antigen components: one or more protective antigens from one or more organisms and an adjuvant. The protective antigen component can be in the form of a whole bacterial culture, a whole virus culture, a cell-free toxoid, a purified toxoid, or a subunit.

When one combines whole cultures of organisms (viruses or bacteria) in a formulation of multicomponent vaccines, the formulation would contain numerous antigens (hundreds to thousands). Some of these are protective antigens as mentioned above. Some of these antigens are detrimental to protection of the animals or cause reaction in the animals ("detrimental antigens"). The detrimental antigens can interfere with the protective antigens by either physically or chemically blocking the active sites of the protective antigens. The interference prevents the protective antigens from protecting animals. Also, the detrimental antigens can produce negative responses such as local reactions, systemic reactions, anaphylaxis and/or immunosuppression in the animals. Therefore, the use of combinations of whole culture organisms can cause problems with efficacy or with animal reactivity. Animal reactivity produces localized reactions resulting in swellings or abscesses at the injection sites or a systemic response such as anaphylaxis that can result in death of the animal.

Aggravating the animal reactivity is the administration of multi-component vaccines to large animals (e.g., cattle) in high doses. The dose range has historically been from about 5 mL to 10 mL to allow incorporation of all of the protective antigens into one formulation. Illustratively, up to seven clostridial whole cultures or toxoids can be combined into a 5.0 mL dose of vaccine for administration to cattle. See, for instance, pages 319, 320, 321, 322, and 432 of the Compendium of Veterinary Products, Third Edition, 1995–1996). Also, 6 Clostridial whole cultures or toxoids have been combined with *Hemophilus somnus* in a 5.0 mL dose vaccines. See pages 191, 192, 319, 433, 490, and 1013 of the Compendium of Veterinary Products, Third Edition, 1995–1996). Reportedly, such vaccines demonstrate significant animal reactivity.

Animal reactivity that produces localized reactions (often called injection site lesions or blemishes) have become a matter of significant concern for the beef industry. Many scientific and lay articles since 1991 have addressed the concern with injection site lesions. See Stokka et al, J. Am. Vet. Med. Assoc., 1994, Feb. 1, 204(3): 415–9, Effertz, Beef Today, March 1991 and Beef Today, September 1992, Dittmer, CALF News Cattle Feeder, September 1992; Smith, FEEDSTUFFS, Aug. 24, 1992, and Hrehocik et al, dvm, September 1992. During the past several years, many scientific and lay articles have reported that injection site lesions are deleterious to the quality of beef. The injection site lesions must be cut out of the meat and discarded. This causes significant monetary loses to retailers, beef packers and feedlots. It has been estimated that 12–15% of prime beef cuts have some type of injection site lesion that must be trimmed away (Effertz, Beef Today, March 1991). This article attributes the main cause of the injection site lesions to 7-way clostridial vaccines. Additionally, there have been reports that up to 90% of cattle have injection site lesions in their carcass. Injection site lesions have been associated with: (1) the presence of many detrimental antigens or contaminants which are present in whole culture vaccines, (2) the adjuvants incorporated into such vaccines, (3) the method of administration of such vaccines (4) the large dose size of some of the multicomponent vaccines (5.0–10.0 mL), and (5) animal the reactivity of the protective antigen components of the vaccines.

Typically, clostridial vaccines are not highly purified because purification can be cost prohibitive. As one would realize, animal vaccine production must be necessarily economically effective if the vaccines are to enjoy widespread use. Therefore, highly purified animal vaccines are virtually cost prohibitive.

Somewhat related prior art involves two vaccines containing six clostridial whole cultures or toxoids administered in a 2.0 mL dose volume. See Compendium of Veterinary Products, Third Edition, 1995–1996, pages 133, 1183, 1184 and 1185 and the advertising brochure entitled "ALPHA-7™-JUST ONCE". However, these vaccines do not include any additional component such as: additional clostridial component(s) or one or more non-clostridial component(s).

Antigenic components of clostridial vaccines were typically obtained by concentrating whole cultures of the bacteria. Concentration was accomplished by precipitating whole cultures with ammonium salts such as ammonium sulfate or concentrating such whole cultures via ultrafiltration. Both procedures are costly. Additionally, these procedures produce massive amounts of cells resulting in a high antigen mass that remains as an antigenic mass of solids in the product. Such a high antigenic mass would induce animal reactivity, particularly injection site lesions.

An even greater problem exists when one combines clostridial organisms with non-clostridial organisms such as Gram-negative bacteria, e.g., *H. somnus* and *M. bovis* and the Pasteurella spp. Many of these organisms are, in themselves, highly reactive and contain high levels of endotoxin that produce anaphylaxis. Also, their antigenic components supposedly cause interference. The high dose of the art-known combination of *H. somnus* and six clostridial components, i.e., a 5.0 mL dose volume can be the source of animal reactivity. In the case of non-clostridial viral formulations, the addition of clostridial components to these formulations can adversely affect viral epitopes. Consequently the viral components of the formulation may become non-efficacious.

Because of the severity of the Clostridial diseases and other disease complexes described herein, it is increasingly important that calves and young cattle entering feedlots as well as pregnant cows are properly vaccinated. The vaccines must contain protective antigens described herein. While one could administer each of the protective antigens in a monovalent vaccine, this mode of administration would require several vaccinations for each animal. This is impractical in a because: 1) handling animals for repeated vaccinations can result in undue stress and consequential diseases; 2) labor for performing such vaccinations is expensive compared to the profit obtained from each animal; 3) the more injection sites on an animal, the more potential for injection site reactions.

There is, therefore, a clear need for multicomponent vaccines containing many protective antigens that do not contain detrimental antigens and do not produce animal reactivity. By this invention, there are provided low dose multicomponent vaccines containing: protective antigen components of a clostridial organism(s) and at least one non-clostridial protective antigen component and an adjuvant, and the processes for making and using the vaccines.

SUMMARY OF THE INVENTION

This invention relates to a multicomponent vaccine comprising: a safe and immunogenically effective combination of protective antigen components from at least one clostridial organism, a protective antigen component from a non-clostridial organism and an adjuvant, wherein the vaccine is in a low dose volume. By "low dose" is meant dose volumes, including the adjuvant which are less than 5.0 mL and which do not adversely affect the protective antigen components or the animal post vaccination. Generally, an antigen is that which produces an antibody response against the antigen, which response is not necessarily protective. By the term "protective antigen" is meant an antigen that produces an immune response and imparts protection to the animal. A vaccine containing such a protective antigen is characterized as "immunogenically effective."

Also, encompassed by the invention is a multicomponent vaccine for ruminants comprising: a safe and immunogenically effective combination of a protective antigen component from at least two and preferably six to seven clostridial organisms; a protective antigen component from a non-clostridial organism and an adjuvant, wherein the vaccine is in a low dose volume.

In the present embodiment of the invention, the multicomponent vaccine comprises a safe and immunogenically effective combination of an antigen component from one or more clostridial organisms; an antigen component from an organism selected from the group consisting of a Gram negative organism, a Gram positive organism, a virus, a parasite and a rickettsia and an adjuvant wherein the vaccine is in a dose size of 3.0 mL or less.

In a preferred embodiment of the invention, the multicomponent vaccine for ruminants comprises a safe and immunogenically effective combination of an antigenic component from six clostridial organisms, which are *Clostridium chauvoei, Clostridium septicum, Clostridium novyi, Clostridium perfringens* type C, *Clostridium perfringens* type D and *Clostridium sordellii*, an antigen component from *H. somnus* or *M. bovis* and an adjuvant, wherein the vaccine is in a dose size of 3.0 mL or less.

In another preferred embodiment of this invention, the multi-component vaccine for ruminants comprises: a safe and immunogenically effective combination of a protective antigen component from seven clostridial organisms which are *Cl. chauvoei, Cl. septicum, Cl. novyi, Cl. perfringens* type C, *Cl. perfringens,* type D, *Cl sordellii,* and *Cl. haemolyticum*; an antigen component from *Haemophilus somnus* or *Moraxella bovis* and an adjuvant, wherein the vaccine is in a dose size of 3.0 mL or less.

In another preferred embodiment of this invention, the multi-component vaccine for ruminants comprises: a safe and immunogenically effective combination of an antigen component from at least two clostridial organisms such as *Cl. perfringens* type C and *Cl. perfringens* type D; an antigen component from a virus such as an infectious bovine rhinotracheitis virus (IBRV) and an adjuvant, wherein the vaccine is in a dose size of 3.0 mL or less.

A particularly preferred embodiment of this invention includes a multicomponent vaccine for ruminants comprising: a safe and immunogenically effective combination of a protective antigen component from more than two clostridial organisms selected from the group consisting of *Cl. chauvoei, Cl. septicum, Cl. novyi, Cl. perfringens* type C, *Cl. perfringens* type D, *Cl sordellii,* and *Cl. haemolyticum*; protective antigen components from viruses which are selected from the group consisting of an infectious bovine rhinotracheitis virus (IBRV), a parainfluenza type 3 virus ($PI_3V$), a bovine virus diarrhea virus (BVDV) and a bovine respiratory syncytial virus (BRSV) and an adjuvant, wherein the vaccine is in a dose size of 3.0 mL or less.

In another particularly preferred embodiment of the invention the multicomponent vaccine comprises: a safe and immunogenically effective combination of a protective antigen component from at least six clostridial organisms; a protective antigen component from a plurality of viruses and an adjuvant, wherein the vaccine is in a dose size of 3.0 mL or less.

The most preferred embodiment of the invention is a multi-component vaccine comprising: a safe and immunogenically effective combination of a protective antigen component from at least seven clostridial organisms; protective antigen components from at least four viruses and an adjuvant, wherein the vaccine is in a dose size of 3.0 mL or less.

Further encompassed by the invention is a method for producing a multicomponent vaccine comprising a safe and immunogenically effective combination of protective antigen components from clostridial organisms and a protective antigen component from a non-clostridial organism and an adjuvant wherein the vaccine is in a dose size of 3.0 mL or less, said method comprising: 1) identifying the protective antigen component of each organism by in vivo or in vitro methods; 2) quantitating the protective antigen components using antigen quantitation assays to provide the protective antigen component in an amount sufficient to produce a protective vaccine with the least antigenic mass; 3) identifying components of the organisms containing detrimental antigens by using the antigen quantitation assays and animal reactivity testing; 4) purifying the protective antigen components which contain detrimental antigens to remove the detrimental antigens; 5) selecting for each organism requiring inactivation, an effective inactivating agent which kills the organism without denaturing the protective antigen component; 6) selecting an effective adjuvant which produces enhancement of immune response without causing unacceptable animal reactivity for each component; 7) adjuvanting the protective antigen components sensitive to the effects of detrimental antigens organisms individually; 8) pooling all protective antigen components.

Also, encompassed by the invention is a process for administering the vaccines of the invention to ruminants.

By the present invention, it has been demonstrated that there is a significant difference in the size of injection site lesions in cattle vaccinated with: (1) a conventional 5.0 mL dose multicomponent clostridial product and (2) the low dose (2.0 mL) multicomponent vaccine of this invention. The area of the injection site lesion produced by the low dose vaccine is significantly smaller, post injection than the lesion produced by the conventional 5.0 mL dose vaccine. The low dose multicomponent vaccine produced injection site lesions in an insignificant number of cattle as compared with the conventional vaccine.

DETAILED DESCRIPTION OF THE INVENTION

In accordance with the invention it has been discovered that in the preparation of multicomponent vaccines such as those containing seven clostridial organisms, one can: identify and reduce the required antigenic mass and combine it with a compatible adjuvant to produce a low dose, safe and immunogenically effective vaccine. This discovery is the basis of the inventive concept described herein. According to this inventive concept, the skilled artisan can combine: protective antigen components from the clostridial organisms and non-clostridial organisms, and an adjuvant in a low dose volume, and safely administer it to ruminants to protect them against diseases described more fully hereunder.

More specifically, the invention relates to a multicomponent vaccine comprising a safe and immunogenically effective combination of: an antigen component from one or more clostridial organisms; an antigen component from a non-clostridial organism selected from the group consisting of a Gram negative organism, a Gram positive organism, a virus, a parasite and a rickettsia and an adjuvant, wherein the vaccine is in a dose size of 3.0 mL or less. Non-limiting examples of the clostridial organisms and diseases in ruminants are as follows:

*Clostridium chauvoei* causes the disease blackleg. This organism, like all Clostridial organisms, produces spores that can survive in soil for years and, during this time, can infect susceptible animals (cattle and sheep) which ingest them. Blackleg is an acute, infectious but noncontagious, disease of cattle and sheep characterized by gaseous tissue swelling, usually in the heavy muscles. The organism enters cattle or sheep via feed or cuts or by shearing, docking, or castration. The onset of the disease is quite sudden. Body temperature rises rapidly and muscular stiffness, depression and reluctance to move are prominent. When infection is extensive, death often occurs within 16–72 hours. Treatment of sick animals is futile since there is often permanent damage done to their meat.

*Clostridium septicum* causes the disease of malignant edema, or gas gangrene, a rapidly extending edematous swelling, in subcutaneous tissues of cattle. The disease is characterized by gangrene and gaseous swelling surrounding a wound. Incidence of the disease often follows castration, dehorning, accidental puncture wounds and lacerations, abortions, and vaccination with unclean needles. The incubation period is short and death occurs within 12 to 48 hours. Death is primarily caused by toxins released by multiplying organisms after infection occurs. As with *Cl. chauvoei*, it is impractical to treat the animals.

*Clostridium novyi* causes the condition of black disease or infectious necrotic hepatitis which is an acute infectious disease of cattle and sheep. The causative spore-forming organism may enter cattle through the digestive tract, lungs or wounds. In areas where liver flukes are endemic, *Cl. novyi* is especially dangerous because the organism will multiply in damaged areas resulting from the migration of liver flukes. The organism multiplies rapidly and produces a highly fatal exotoxin causing toxemia and death. Death is usually sudden with no well-defined signs. Because of the rapidity of death, treatment is not practical.

*Clostridium sordellii* causes a disease similar to *Cl. novyi* and *Cl. septicum*. The organism is an inhabitant of the soil and of the animal intestine. Most infections by the organisms are associated with wounds or liver flukes. Lesions at the site of the infection progress rapidly, followed by fever, depression and edema that is similar to that produced in *Cl. novyi* infections. A rank odor is detected in diseased tissues. Death is also sudden indicating that treatment is not practical.

*Clostridium perfringens* types B, C, and D are found as spores in the soil but are also parts of the normal intestinal flora of healthy animals. Under favorable conditions, such as when animals are being fed high protein diets in feedlots, the organisms multiply rapidly in the intestines. They produce lethal toxins which kill infected animals. *Cl. perfringens* type B causes sudden death in cattle and lambs. *Cl. perfringens* type C produces an acute hemorrhagic enteritis in calves, lambs, piglets and older cattle and sheep on high-energy feeds. *Cl. perfringens* type D causes overeating disease in feedlot cattle unaccustomed to high-energy concentration rations. All of the syndromes produced by the various types of *Cl. perfringens* have rapid onset and result in death before the animals can be effectively treated.

*Clostridium tetani* causes tetanus that can afflict all mammals.

The disease results from organisms entering their body via puncture wounds. As the organisms multiply, toxins which affect the central nervous system are produced. Infected animals become stiff, have difficulty swallowing and breathing, and are afflicted with spasmodic contractions of the musculature. While treatment with antitoxin is viable, it is extremely expensive and cost inefficient.

As set forth above, the non-clostridial organism can be selected from the group consisting of: a Gram negative organism, a Gram positive organism, a virus, a parasite and a rickettsia. The following is a non-limiting illustration of the Gram negative organisms.

*Haemophilus somnus* (*H. somnus*) is an organism that causes a complex of disease conditions found mainly in feedlot cattle The disease is, also, found in dairy and pasture cattle. This organism can cause a thromboembolic meningoencephalitis (TEME), a respiratory tract disease, reproductive diseases and a general septicemia. It is a non-motile, rod-shaped bacterium which is difficult to isolate and is most likely spread by respiratory secretions and discharges. Its incubation period is two to seven days. Infected animals can be treated successfully with antibiotics if they are treated early enough in the course of the disease. Unfortunately, once the infection becomes systemic, antibiotic effectiveness is decreased. Vaccination is the best method for protecting a herd of cattle from these *H. somnus*-induced diseases. The fact that *H. somnus* is a Gram-negative organism, and therefore contains endotoxin, renders the formulation of a non-reactive vaccine difficult. *Moraxella bovis* (*M. bovis*) is a Gram-negative organism that causes pink-eye in cattle. This disease is often chronic in herds of cattle and causes cattle to develop keratoconjunctivitis, with blindness a sequelae, after a period of time. Treatment is expensive as it must be continued for long periods of time. *M. bovis* has the potential to cause anaphylaxis and/or severe local reactions.

*Campylobacter fetus* is a Gram-negative organism that causes a venereal disease transmitted during breeding. Although the disease is often subclinical, it causes temporary infertility, irregular estrous cycles, delayed conception and, occasionally, abortion in cows.

Leptospira spp. infect and localize in the kidneys and are shed in the urine. Infection with Leptospira spp. can cause anemia, bloody urine, fever, loss of appetite and prostration in calves. Infection is usually subclinical in adult cattle. Infected pregnant cows, however, often abort, and dairy cows may exhibit a marked decrease in milk production. There are at least six major serovars in the species *L. interrogans* (*L. pomona, L. canicola, L. grippotyphosa, L. icterohaemorrhagiae, L. hardjo*, and *L. bratislava*),

*Pasteurella haemolytica* and *Pasteurella multocida* are causative agents of bovine pneumonia in feedlot cattle and young calves. They are the most significant components of the shipping fever complex and induce clinical pneumonia in cattle which are predisposed to infections with: infectious bovine rhinotracheitis, parainfluenza type 3 virus, bovine respiratory syncytial virus or bovine virus diarrhea virus. Infectious bovine rhinotracheitis virus causes a severe respiratory infection of cattle, specifically in feedlot conditions. The disease is characterized by: high temperature, excessive nasal discharge, conjunctivitis and ocular discharge, inflamed nasal mucosa, increased rate of respiration, coughing, loss of appetite, depression and/or reproductive failure in cattle. Infection with this virus often predisposes cattle to bacterial infections that cause death.

Parainfluenza type 3 virus ($PI_3$) usually causes a localized upper respiratory tract infection, producing elevated temperatures and moderate nasal and ocular discharge. Although clinical signs of $PI_3$ are typically mild, this infection weakens the respiratory defenses and allows replication of other pathogens, particularly Pasteurella spp.

Bovine virus diarrhea (BVD) is a major cause of abortion, fetal resorption or congenital fetal malformation. If susceptible cows are infected with non cytopathic BVD virus during the first trimester of pregnancy, their calves may be born persistently infected with the virus. Exposure of those calves to certain virulent cytopathic BVD virus strains may precipitate BVD-mucosal disease. Clinical signs of this disease include loss of appetite, ulcerations in the mouth, profuse salivation, elevated temperature, diarrhea, dehydration and lameness. The disease usually affects feedlot cattle.

Bovine respiratory syncytial virus (BRSV) infects cattle of all ages and causes: rapid breathing, coughing, loss of appetite, discharge from the nose and eyes, fever and swelling in the cervical area. In an acute outbreak, death may follow 48 hours after the onset of signs.

The following is a non-limiting illustration of the parasites that are employed herein.

Neospora spp. have been recently isolated form aborted fetuses. These organisms are parasites which have been proposed as a major cause of abortion in pregnant cows throughout the world. If this proves to be correct, a vaccine for protection of pregnant cattle against Neospora spp. could be a requirement in the future.

In accordance with the invention, clostridial organisms can be
selected from the group consisting of: *Cl. chauvoei, Cl. septicum, Cl. novyi, Cl. perfringens* type C, *Cl. perfringens* type D, *Cl sordellii*, and *Cl. haemolyticum*. Preferably, the protective antigen of the clostridial component is derived from six to seven clostridial organisms.

The non-clostridial protective antigen component can be selected from the group consisting of Gram negative bacteria, Gram positive bacteria, viruses, parasites, rickettsia and a combination thereof. Non-limiting examples of the Gram negative organisms can be selected from the group consisting of: *H. somnus, M. bovis, E. coli, Salmonella typhimurium, Pasteurella hemolytica, Pasteurella multocida, Campylobacter fetus*, Leptospira spp and a combination thereof. Preferred herein are *H. somnus* and *M. bovis*.

Non-limiting examples of the Gram positive organisms are *Clostridium tetani, Bacillus anthracis, Listeria monocytogenes, Actinomyces pyogenes* and a combination thereof.

Non-limiting examples of the virus can be selected from the group consisting of: infectious bovine rhinotracheitis (IBRV), parainfluenza virus type 3 ($PI_3V$), bovine virus diarrhea virus (BVDV) bovine respiratory syncytial virus (BRSV) and a combination thereof.

Non-limiting examples of the parasites are Neospora spp., *Tritrichimonas foetus*, Cryptosporidia spp. and a combination thereof.

A non-limiting example of the rickettsia is *Ehrlichia bovis*.

In accordance with the invention, the clostridial and non-clostridial protective antigen components can be in the form of: inactivated or modified live whole cultures, toxoids, cell-free toxoids, purified toxoids, subunits or combinations thereof.

Adjuvants useful herein are by definition chemical compounds added to vaccines to enhance the production of an immune response by the animal receiving the vaccine. Most adjuvants function by: (1)producing an irritation at the site of injection causing leukocytes (immune cells) to infiltrate the area, and/or (2) by producing a depot effect—holding the antigen(s) at the injection site for as long as possible. If infiltration of leukocytes to the injection site is extensive, swelling and injection-site lesions will occur. Such leukocytes carry the antigens from the vaccine to cells within the immune system (of the vaccinated animal) which can produce a protective response. Some newer polymer adjuvants function by encapsulating antigens and releasing them slowly over a period of weeks or months. These newer adjuvants can help in protecting antigens from interference and are generally less likely to cause extensive infiltration of leukocytes to the injection site. In accordance with the invention, the adjuvants can be selected from the group consisting of: oil-in-water, water-in-oil, $Al(OH)_3$, $Al_2(SO_4)_3$, $AlPO_4$, extracts of bacterial cell walls (Mycobacterium, Propionibacterium, etc.), extracts of plants (acemannan, saponin or QUIL A), polymers, including block copolymers, liposomes and combinations thereof. Preferred herein are adjuvants that function by encapsulating antigens and releasing them slowly over a period of weeks or months Preferably, the adjuvants are polymers, including block copolymers (alternately referred to herein as polymer adjuvants. A specific example of the preferred adjuvant is carbopol. Generally, the more effective the adjuvant is, the more irritating it is and the more likely it is to cause an animal reaction. It is a distinct feature of the invention that effective adjuvants can be formulated with the protective antigens to produce vaccines that are safe and effective.

It is also a distinct feature of the invention that a multicomponent vaccine for ruminants would include all the required protective antigen components and adjuvant, in a low dose. In essence, fewer than five protective antigens from each organism would be required to make a vaccine immunogenically effective. However, a vaccine containing only the protective antigens would be essentially a very pure vaccine. Because of the high purity of the antigens, it would be difficult adjuvant them with commonly used adjuvants. The pure antigen would require adjuvants that are different from the typical adjuvants. Therefore, a commercial scale production of clostridial vaccines containing very pure protective antigen components would be technically difficult. At any rate, the preparation of a very pure animal vaccine on a commercial scale is prohibitive because of the cost of purification.

In accordance with the invention, individual components of the multicomponent vaccines described herein can be formulated with protective antigens derived from: whole culture bacteria, whole culture viruses, cell-free toxoids, purified toxoids and/or subunits. Whole cultures contain numerous antigens. Some of the antigens impart protection (protective antigens), some produce negative response (detrimental antigens) and some are essentially neutral (neutral antigens). Subunits can be obtained from the organisms themselves by conventional methods such as: centrifugation, ultrafiltration, and extraction with detergents or organic solvents. Alternately, the subunits can be produced by recombinant technology and expressed in live vectors or other organisms and isolated and purified. It would be understood that protective antigen components may contain few to many antigens at least one of which is protective or immunogenically effective.

In the preparation of the vaccine of the invention, one can incorporate protective antigen components from a plurality of organisms. This occasions the likelihood of one protective antigen component interfering with another. This is particularly the case if the protective antigens are derived from clostridial organisms. The interference may result from: (1) physical masking or hiding of an active site of one protective antigen component by another, (2) aggregation or agglomeration of one or more protective antigen components so that one or more active sites are hidden from the immune system, (3) chemical interaction wherein there is a change in the active site of one protective antigen component by another. The latter change can result from a toxic effect, chemical binding or a conformational change in a critical portion of an active site.

It is a distinct feature of the invention that the effects of the detrimental antigens can be avoided by the process of the invention. The process comprises: using specialized procedures for identifying the protective antigen components; quantitating the protective antigen components; identifying those protective antigen components that contain detrimental antigens; purifying those protective antigen components that contain detrimental antigens to remove such detrimental antigens; selecting adjuvants that produce the necessary enhancement of the immune response without causing unacceptable reactivity and protect against interference; individually adjuvanting the protective antigen components that are sensitive to the effects of detrimental antigens; pooling the various protective antigen components into a low dose volume vaccine.

In the preparation of the multicomponent vaccines, the inventors employ adjuvant that protect the active sites of the various protective antigen components. In effect, the adjuvants interact with targeted protective antigens, and not other antigens. As would be realized, the selection of an adjuvant is critical. The adjuvant must be one that is potent enough to produce significant enhancement of the immune response without producing unacceptable local or systemic reactions. The term "produce significant enhancement of the immune response" refers to stimulation of the immune system such that protection of the host animal results from vaccination. Additionally, the adjuvant must reduce or prevent the interference with the protective antigens. An adjuvant that encapsulates antigens is preferred. This characteristic is usually associated with polymer- or block copolymer-type adjuvants. The preferred adjuvant for this invention is one containing "CARBOPOL" or the equivalent thereof.

An integral part of the invention is the use of a specified test method for antigen quantitation of the protective antigen components. Illustratively, the test method for quantitation of a clostridial protective antigen component involves injection of mice with combinations of antigen and specific antisera. The test method is referred to herein as "a combining power test". The resultant measurement of antigen is designated as "combining power unit" (CPU). The CPU test, developed in accordance with the invention, is an integral part of the formulation of combination clostridial products. The test comprises adding varying volumes of test material to a series of tubes. The total volume of test material in each tube is brought to 1.0 mL using Peptone Sodium Chloride Diluent [8.5 gm Sodium Chloride and 10 gm Bactone Peptone/liter (PND)]. One half milliliter of PND containing one International Unit of antitoxin, obtained from the clostridial organism being tested, plus enough excess antitoxin to neutralize approximately 100 MLD of toxin, is added to each tube. The tubes are mixed and 18 to 20 gm mice are inoculated intravenously with 0.5 mL from each tube. The mice are observed for 48 hours and death is recorded. The CPU of the test material is calculated as follows:

$$\text{CPU/mL} = \frac{\text{Reciprocal of the dilution of the toxoid} \times 2}{\text{Smallest volume of the above dilution which kills 100\% of inoculated mice}}$$

Other test methods that produce substantially the same results as described herein are encompassed by the claimed invention. Non-limiting examples of other test methods can be ELISA assays and liquid chromatography, which quantitate antigens directly in vaccines. In accordance with the foregoing, the skilled artisan can employ the required CPU/mL or the equivalent Elisa antigen quantitation unit to ascertain the value of the amounts of the antigenic components that are useful in making and using the vaccines of the invention.

The inventors have unexpectedly found that multicomponent vaccines containing a plurality of clostridial protective antigen components plus at least one non-clostridial protective antigen component and an adjuvant in a low dose volume can be produced by: identifying the protective antigen component of each organism by in vivo or in vitro methods; quantifying the protective antigen components during formulation and manufacture of the vaccine, using antigen quantitation assays described above to provide the protective antigen component in an amount sufficient to produce a protective vaccine with the least antigenic mass; identifying the antigenic components of the organisms which contain detrimental antigens by using the antigen quantitation assays and animal reactivity testing; purifying the protective antigen components which contain detrimental antigens to remove such antigens; selecting the inactivating agent for each organism requiring inactivation such that the organism is killed without denaturing the protective antigen component; selecting an adjuvant for each protective antigen component that requires an adjuvant by evaluating the adjuvant's ability to enhance the immune response to the specific protective antigen component without causing unacceptable animal reactivity; adjuvanting, individually, the protective antigen components that require such adjuvanting; pooling the protective antigenic components into a low dose vaccine that imparts protection to animals to which the vaccine is administered. By this method, one can produces a commercially-viable, cost effective safe, immunogenically effective multicomponent vaccine. The multicomponent vaccine contains a combination of: one or more clostridial protective antigen components with one or more non-clostridial protective antigen components and an adjuvant within a low dose volume of 3.0 mL or less. The use of multicomponent vaccines, i.e., commercial scale vaccines of this infection, do not produce significant injection-site lesions upon subcutaneous or intramuscular administration.

The following is a specific description of the invention that is intended to assist those skilled in the practice of the invention. More specifically, the description relates to the characterization of the antigenic components and the manner in which they are formulated, including inactivation and adjuvanting.

Cl. chauvoei protective antigens have been found by the inventors to be associated with cells. These protective antigens are not found in proteinaceous material excreted into the culture supernatant while the organism is being grown in fermenters. It has also been found that the Cl. chauvoei protective antigen component does not interfere with other protective antigen components in the multicomponent clostridial vaccine. Therefore, a whole cell bacterin or a cell extract can be used. The whole cell bacterin or cell extract may be inactivated with formaldehyde (0.05–1.5%), Betapropriolactone (BPL) at 0.05 to 0.3% or Binary ethyleneimine (BEI) at 0.05 to 0.3%. After inactivation, this component must be adjuvanted separately. If BPL or BEI are used for inactivation they must be neutralized prior to adjuvanting. Adjuvants which enhance this C protective antigen component are Al(OH)$_3$, oils, saponin, QUIL A, block co-polymers and polymers such as "CARBOPOL". Oil adjuvants can be used as co-adjuvants with polymers. CARBOPOL is more preferred and is added to the inactivated whole culture at a low pH. The pH is then adjusted upward to approximately 7.0 with, say, sodium hydroxide (NaOH). This pH adjustment step allows for the protective antigen components of the Cl. chauvoei to become encapsulated in the polymer adjuvant. Without being bound to any particular theory of the invention, it is believed the Cl. chauvoei antigens are released over a period of several weeks. Because of the slow release, these antigens do not cause the typical animal reaction. The long-term release causes an enhanced immune response by the vaccinated animal.

The protective antigen component of Cl. septicum is associated both with the cell and with a toxin. The toxin is secreted into a supernatant while the organism is growing. Therefore, this protective antigen component is derived from the cell and supernatant. Apparently, Cl. septicum does not interfere with other protective antigen components in multicomponent clostridial vaccines containing non-clostridial protective antigen components. The whole cell bacterin or cell extract can be inactivated with formaldehyde (0.05–1.5%), BPL (0.05–0.3%) or BEI (0.05–0.3%). After inactivation, this protective antigen component must be adjuvanted separately. When BPL or BEI are used for inactivation, they must be neutralized before adjuvanting. Adjuvants that enhance this protective antigen component can be: Al(OH)$_3$, oils, saponin, QUIL A, block co-polymers and polymers such as CARBOPOL. Oil adjuvants can be used if combined as co-adjuvants with polymers. The preferred adjuvant are the polymer adjuvant. Preferably, the adjuvant is added to the inactivated whole culture at a low pH. Then the pH is adjusted upward to approximately 7.0 with NaOH. This pH adjustment step increases the pH from approximately 5.0 to 7.0 during which the antigens of the Cl. septicum become encapsulated in the CARBOPOL. The resulting vaccine does not cause the typical animal reactivity but releases the Cl. septicum antigens over a period of several weeks. This mode of release causes an enhanced immune response by the vaccinated animal.

The protective antigen component of Cl. novyi, is believed by the inventors to be associated with a cell protein, and a toxin that is excreted into a supernatant. Therefore, this protective antigen component is derived from both the cell and supernatant, in either concentrated or non-concentrated form. Apparently, the protective antigen of the Cl. novyi does not interfere with other protective antigen components in multicomponent clostridial vaccines when combined with non-clostridial protective antigen components. The whole cell bacterin or cell extract may be inactivated with formaldehyde (0.05–1.5%), BPL (0.05–0.3%) or BEI (0.05–0.3%) and must be adjuvanted separately. If BPL or BEI is used, it must be neutralized before adjuvanting. Adjuvants that enhance this protective antigen component are Al(OH)$_3$, oils, saponin, QUIL A, block co-polymers and polymers such as CARBOPOL. Oil adjuvants can be used if combined as co-adjuvants with polymers. The CARBOPOL polymer adjuvants are preferred. The polymer adjuvant is added to the inactivated whole culture at a low pH. Then the pH is adjusted upward to approximately 7.0 with NaOH. This pH adjustment step increases the pH from approximately 5.0 to 7.0 during which the antigens of the Cl. novyi become encapsulated in polymer. The resulting vaccine does not cause the typical animal reactivity but releases the Cl. novyi antigens over a period of several weeks. The long-term release causes an enhanced immune response by the vaccinated animal.

The protective antigen component of Cl. sordellii is believed to be associated with a toxin that is secreted into the supernatant as the culture is growing. Therefore, this protective antigen component is derived from the supernatant. This protective antigen component is typically concentrated via ultrafiltration through a 10,000 dalton molecular weight (MW) cartridge before adjuvanting. The Cl. sordellii toxin may be inactivated with formaldehyde (0.05–1.5%), BPL (0.05–0.3%) or BEI (0.05–0.3%) prior to adjuvanting, and must be adjuvanted separately. If BPL or BEI is used for inactivation, it must be neutralized before adjuvanting. Adjuvants that enhance this protective antigen component are Al(OH)$_3$, oils, saponin, QUIL A, block co-polymers and polymers such as CARBOPOL. Oil adjuvants can be used if combined as co-adjuvants with polymers. The polymer adjuvant is are preferred. The CARBOPOL polymer adjuvant is added to the inactivated whole culture at a low pH. Then the pH is adjusted upward to approximately 7.0 with NaOH. This pH adjustment step increases the pH from approximately 5.0 to 7.0 during which the antigens encapsulated in polymer adjuvant. The resulting vaccine does not cause the typical animal reactivity but releases the Cl. sordellii antigens over a period of several weeks. The long-term release causes an enhanced immune response by the vaccinated animal.

The protective antigen components of Cl. perfringens types C and D are known to be toxoids that are excreted by the cells. Because they cross-protect against *Cl perfringens* type B, these protective antigen components only need to contain cell-free supernatant containing inactivated toxin (toxoid). These two components are considered to represent 3 components (B,C, and D). In formulations of a multicomponent clostridial vaccine, one may use *Cl. perfringens* types C and D protective antigen components that contain cells or have the cells removed therefrom (cell free toxoid). Before the removal of the cells, the whole culture is harvested from the fermenter and inactivated with formaldehyde (0.5–1.5%), BPL (0.05–0.5%) or BEI (0.05–0.5%) and before adjuvanting. The cells can be removed by, say, filtration or centrifugation, In either case, the respective antigens must be adjuvanted separately. If BPL or BEI is used for inactivation, it must be neutralized before cell removal. Adjuvants which enhance this protective antigen component are $Al(OH)_3$, oils, saponin, QUIL A, block co-polymers and polymers such as CARBOPOL. Oil adjuvants can be used if combined as co-adjuvants with polymers. Preferred here is the polymer adjuvant. The CARBOPOL adjuvant is added to the inactivated whole culture at a low pH. Then the pH is adjusted upward to approximately 7.0 with NaOH. This pH adjustment step increases the pH from approximately 5.0 to 7.0. During this increase the protective antigen components of the *Cl. perfringens* become encapsulated in the polymer adjuvant.

The protective antigen component of *Cl. haemolyticum* is believed to be both cell-associated and excreted as a toxin into the supernatant. Therefore, this protective antigen component contains antigens from the cells and supernatant. Because of its high cell mass, this protective antigen component can cause interference with other protective antigen components of a multicomponent clostridial vaccine. Typically, this protective antigen is concentrated by, say, ultrafiltration with a 10,000 molecular weight cartridge before adjuvanting. The *Cl. haemolyticum* whole culture can be inactivated with formaldehyde (0.05–1.5%), BPL (0.05–0.3%) or BEI (0.05–0.3%) before concentration. The inactivated, concentrated material must be adjuvanted separately. If BPL or BEI are used for inactivation, it must be neutralized prior to adjuvanting. Adjuvants which enhance this protective antigen component are $Al(OH)_3$, oils, saponin, QUIL A, block co-polymers and polymers such as CARBOPOL. Oil adjuvants can be used if combined as co-adjuvants with polymers. Preferred herein is the polymer adjuvant. The CARBOPOL adjuvant is added to the inactivated whole culture at a low pH. Then the pH is adjusted upward to approximately 7.0 with NaOH. This pH adjustment step increases the pH from approximately 5.0 to 7.0. During the increase, the protective antigen components of the *Cl. haemolyticum* become encapsulated in polymer adjuvant. The resulting vaccine does not cause the typical animal reactivity but releases the *Cl. haemolyticum* antigens over a period of several weeks. The long-term release causes an enhanced immune response by the vaccinated animal.

With the foregoing description and the examples to follow, it would be within the purview of the skilled artisan to make and use the low dose, multicomponent vaccines of the invention. In the practice of the invention, the multicomponent, low-dose vaccines can be administered subcutaneously or intramuscularly to protect animals without causing significant injection-site lesions.

This and other aspects of the invention are further illustrated by the following non-limiting examples.

EXAMPLES

Example 1A

This example illustrates the embodiment of this invention comprising a combination of protective antigen components from at least 6 clostridial organisms with protective antigen components from at least 1 non-clostridial component such as a Gram-negative organism. First a multi-component bacterin was formulated with a combination of protective antigen components derived from: *Cl. chauvoei, Cl. septicum, Cl. novyi, Cl. sordellii, Cl. perfrinqens* types C and D; a protective antigen component from *H. somnus* and a carbopol adjuvant. The *H. somnus* protective antigen component was purified enough to prevent animal reactivity but not so much as to make it non-cost effective. Two isolates of *H. somnus* were used in the experiments. One isolate was designated 8025T and the other was designated 14767. Each isolate was grown separately in 160 L of media containing the following components: Pancreatic Digest of Casein, Yeast Extract, Proteose Peptone, NaCl, and $Na_2HPO_4$. The growth medium was supplemented with 0.5% dextrose and 10% horse serum. Dissolved oxygen was controlled during the fermentation cycle at approximately 10% (between 5% and 20%). Fermenters were inoculated with either 3.5% seed (isolate 14767) or 5% seed (isolate 8025T). Cultures were incubated at 37° C., with pH control between 7.1 and 7.3 and allowed to grow until optical densities (absorbance at 540 nm) reached approximately 1.20 (5–24 hours) at which time cultures were inactivated with 0.3% formalin. Inactivation of the *H. somnus* was done with formaldehyde (0.05–1.5%), BPL (0.05–0.5%) or BEI (0.05–0.5%) prior to concentration and adjuvanting. In the use of BPL and BEI, they were neutralized before being used for inactivation. CARBOPOL was added to the inactivated whole culture at a low pH. Then the pH was adjusted up to 7.0 with NaOH. Following inactivation, the whole bacterial cultures were concentrated 10× using a 0.1 micron ultrafiltration cartridge, followed by diafiltration with 11 volumes of Phosphate Buffered Saline (PBS). The washed concentrates were then centrifuged at 7000 RPM using a Sorvall RC5B refrigerated centrifuge and the pellets were resuspended in 100 mL of chilled PBS. Centrifuged concentrates were adjusted to either 10× or 20× concentration (based on initial whole culture volume) and adjuvanted with 10% v/v 10× modified CARBOPOL adjuvant. This adjuvant was comprised of: up to 0.25% CARBOPOL 934P, Tween 80, Span 20 and Cotton Seed Oil. For further experimentation, a 1× dose of *H. somnus* 8025T consisted of either 0.061 mL of adjuvanted *H. somnus* 8025T 20× concentrate or 0.122 mL of adjuvanted 10× concentrate. Likewise, a dose of *H. somnus* 14767 consisted of either 0.061 mL of adjuvanted 20× concentrate or 0.122 mL of adjuvanted 10× concentrate. These volumes corresponded to the amount of antigen contained in 1.0 mL of 14767 or 8025T whole culture, each having an optical density of 1.3 at 540 nm.

Relative purity of the above-described *H. somnus* preparations was demonstrated by comparing their endotoxin levels after the various purification steps. The preparations were compared to whole culture *H. somnus*. Samples of *H. somnus* 8025T and 14767 10× concentrates were removed at various stages in the purification process and diluted to 1× with PBS.

Endotoxin assays were run on the samples using an automated BioWhitaker apparatus and results were normalized against an *E. coli* LPS standard prepared to contain one million endotoxin units per mL. Results are shown in TABLE 1. Results show that the *H. somnus* cultures can be purified using centrifugation or a combination of ultrafiltration and diafiltration. The resultant cultures had endotoxin levels that were less than 10% of those seen in original inactivated whole cultures. This level of endotoxin reduction is adequate to eliminate significant animal reactivity and is cost effective.

TABLE 1

ENDOTOXIN LEVELS OF PURIFIED H. somnus CONCENTRATES

| MATERIAL TESTED | ENDOTOXIN UNITS/mL (X 1000) | |
| --- | --- | --- |
| | ISOLATE 14767 | ISOLATE 8025T |
| INACTIVATED 1X WHOLE CULTURE | 5266 | 8705 |
| 10X CONCENTRATE, DIAFILTERED WITH 11 VOLUMES PBS, RECON. TO 1X | 681 | 1332 |
| 10X CONCENTRATE, DIAFILTERED WITH 11 VOLUMES PBS, CENT., RECON. TO 1X | 422 | 397 |
| 10X CONCENTRATE, CENT., RECONSTITUTED TO 1X | 408 | 397 |
| CENTRIFUGED WHOLE CULTURE, RECON. TO 1X | 431 | 256 |

Example 1B

This example illustrates that immunogenicity is maintained when only the cells were used to produce the protective antigen components. After the purification of *H. somnus* as described in Example 1A, the washed-cell preparations thereof were formulated at various antigen concentrations with a plurality of clostridial protective antigen components and tested as either a 2.0 mL dose or a 5.0 mL dose (positive control) in a mouse vaccination/challenge test [approved by the U.S. Animal Plant Health Inspection Service (APHIS)]. The test was conducted by vaccinating mice with a fractional dose of the test product, boosting such mice with the same dose at 14 days post vaccination and challenging such mice with a virulent *H. somnus* culture at 10–14 days post booster. The challenge culture was mixed with an equal volume of 7% gastric mucin prior to injection. The resulting mixture was strong enough to kill 80% of the control mice (16 of 20). For a satisfactory test, at least 14 of 20 vaccinated mice must survive. The clostridial fractions were produced as follows:

Although any commercial *Cl. chauvoei* whole bacterial culture could be used as the protective antigen component, for purposes of this experiment the *Cl. chauvoei* was grown under strict anaerobic conditions in large-scale fermenters under pH control conditions between 6.5 and 7.6; inactivated with 0.5% formaldehyde and adjuvated with the modified CARBOPOL adjuvant as a separate non-concentrated whole bacterial culture. The modified CARBOPOL adjuvant was the same as that described in Example 1A. The adjuvant was added in a 10% v/v ratio to the *Cl. chauvoei* whole bacterial culture, mixed to allow complete contact with adjuvant while at a low pH, and then pH adjusted to approximately 7.0 with 5 or 10N NaOH.

Although it is expected that any commercial *Cl. septicum* whole culture bacterial culture could be used as the protective antigen component, for purposes of this experiment the *Cl. septicum* was grown under strict anaerobic conditions in large-scale fermenters with pH control between 6.5 and 7.6; inactivated with 0.5% formaldehyde, concentrated minimally using a 10,000 dalton MW ultrafiltration system and adjuvated with the modified CARBOPOL adjuvant by adding the adjuvant directly to the concentrated whole bacterial culture *Cl. septicum*. The modified CARBOPOL adjuvant is the same as that described previously. The adjuvant was added in a 10% v/v ratio to the *Cl. septicum* concentrate, mixed to allow complete contact with adjuvant at the low pH, and then pH adjusted to approximately 7.0 with 5 or 10N NaOH.

*Cl. novyi* was grown under strict anaerobic conditions in large-scale fermenters with pH control between 6.5 and 7.6, inactivated with 0.5% formaldehyde and adjuvated as a non-concentrated whole bacterial culture with the modified CARBOPOL adjuvant as described previously. The adjuvant was added in a 10% v/v ratio to the *Cl. novyi* whole bacterial culture, mixed to allow complete contact with adjuvant at low pH, and then pH adjusted to approximately 7.0 with 5 or 10N NaOH. Combining Power Unit (CPU) was measured, as described above, in the culture post inactivation and post adjuvanting. The CPU of the final protective antigen component was adjusted to 10 CPU/mL with adjuvated PBS.

*Cl. sordellii* was grown under strict anaerobic conditions in large-scale fermenters with pH control between 6.5 and 7.6. At the end of the growth phase, the culture was maintained at a pH of approximately 8.0 for 8–10 hours to facilitate cell lysis. The lysed culture was then inactivated with 0.5% formaldehyde (lysed toxoid), concentrated using a 10,000 dalton MW ultrafiltration cartridge and adjuvated with the modifiede CARBOPOL adjuvant described previously. The adjuvant was added in a 10% v/v ratio to the *Cl. sordellii* lysed toxoid, mixed to allow complete contact with adjuvant at the low pH, and then pH adjusted to approximately 7.0 with 5 or 10N NaOH. After adjuvanting, the combining power was measured and the protective antigen component was adjusted to 100 CPU/mL by dilution with adjuvated PBS.

*Clostridium perfringens* types C and D were grown under strict anaerobic conditions in large-scale fermenters with pH control between 7.3 and 7.5 for 4–8 hours. The whole bacterial cultures were inactivated with 0.5% formaldehyde. For purposes of this experiment, cells were removed by centrifugation in a Sorvall centrifuge at 7000 RPM. The remaining supernatants contained *Cl. perfringens* C or D toxoids. The toxoids were individually concentrated by ultrafiltration through a 10,000 dalton MW cartridge and the concentrates were assayed for their quantity of protective antigen component by the previously-described combining power test. After adjustment of the antigen concentration (CPU), each protective antigen component was individually adjuvated using the modified CARBOPOL adjuvant described previously. The adjuvant was added in a 10% v/v ratio to the individual *Cl. perfringens* toxoids (C or D), mixed to allow complete contact with adjuvant at the low pH, and then pH adjusted to approximately 7.0 with 5 or 10N NaOH.

*Cl. haemolyticum* was grown under strict anaerobic conditions in large-scale fermenters with pH control between 6.8 and 7.3. The culture was harvested and inactivated with 0.5% formaldehyde prior to concentration. A 10,000 dalton MW ultrafiltration cartridge was used to concentrate the whole culture which was then adjuvated with the modified CARBOPOL adjuvant described in Example 1A. The adjuvant was added in a 10% v/v ratio to the *Cl. haemolyticum* culture concentrate, mixed to allow complete contact with adjuvant at low pH, and then pH adjusted to approximately 7.0 with 5 or 10N NaOH.

*H. somnus* was prepared according to the description in Example 1A. The pre-adjuvanted clostridial components, as afore-described, were formulated into one pool as shown in TABLE 2. To this pool was added the adjuvanted *H. somnus* component and adjuvanted PBS to equal the dose size being tested.

Experimental serials were made with varying amounts of *H. somnus* washed cell suspension, as described in Example 1A, in combination with 6 or 7 clostridial protective antigen components, in order to determine whether the potency of this component was adversely affected by the purification process or by the mixture of the more purified *H. somnus* with the clostridial components. Serials of product containing 6 clostridial protective antigen components plus *H. somnus* or 7 clostridial protective antigen components+*H. somnus* were prepared as shown in Table 2 and tested for potency of the *H. somnus* protective antigen component according to the mouse test described in Example 1A. Host animal doses of 5.0 mL and 2.0 mL were tested. The results of these tests are shown in TABLE 3 along with a listing of dose size tested and the amounts of *H. somnus* per dose.

This experiment demonstrates that the protective antigens of *H. somnus* are associated with the cells and not with the supernatant which contains the endotoxins. Additionally, the washed cell suspension did not appear to be adversely affected by the 6 clostridial protective antigen components. The *H. somnus* protective antigen component was still potent when the washed cells were resuspended to a concentration equal to one-half the concentration of the original whole culture and mixed with 6 clostridial protective antigen components. When *Cl. haemolyticum* was added to the 6 original clostridial protective antigen components it appeared to adversely affect the *H. somnus* protective antigen component only slightly—not enough to require a dose size greater than 2.0 mL. Therefore, it is commercially feasible to produce a vaccine with protective antigen components from 7 clostridial organisms in combination with a protective antigen component from a Gram-negative organism such as *H. somnus*.

TABLE 2

| ORGANISM | GENERAL COMPONENT FORMULATIONS-PREADJUVANTED: MINIMUM AMOUNT OF COMPONENT/DOSE | ACTUAL VOLUME OF COMPONENT/DOSE | DESCRIPTION OF ANTIGEN |
|---|---|---|---|
| *Cl. chauvoei* | >0.2 mL of WC* | 0.2 mL | WC Nonconc. |
| *Cl. septicum* | 0.11 mL of WC* | 0.11 mL | WC 7.4X Concentrate |
| *Cl. novyi* | 2.0 CPU | 0.2 mL @ 10 CPU/mL | 2.0 CPU Toxoid + WC |
| *Cl. sordellii* | 27.0 CPU | 0.27 mL @ 100 CPU/mL | 27.0 CPU Toxoid + WC |
| *Cl. hemolyticum* | 20 mL equivalents of whole culture | 0.28 mL | 7.2X Conc. Toxoid + WC |
| *Cl. perfringens* type C | 600 CPU/dose | 0.375 mL of whole culture = 600 CPU/dose | WC Nonconc. Purified |
| *Cl. perfringens* type D | 359 CPU/dose | 0.39 mL of whole culture = 350 CPU/dose | WC Nonconc. Purified |
| Adjuvanted PBS | N/A | Amt. needed to bring total dose to volume required | N/A |

*WC = Whole Culture

TABLE 3

POTENCY TESTING OF THE PURIFIED *H. somnus* COMPONENT WHEN COMBINED WITH CLOSTRIDIAL COMPONENTS

| SERIAL NUMBER | TYPE OF PRODUCT | DOSE SIZE (mL) | AMOUNT OF *H. Somnus* PER DOSE*: ISOLATE 8025T | ISOLATE 14767 | POTENCY TEST RESULT (PROTECTED MICE/TOTAL INFECTED) |
|---|---|---|---|---|---|
| 1093-1 | 6-WAY + *H.somnus* | 5.0 | 0.183 1.5X | 0.183 1.5X | 20/20 |
| 1093-2 | 6-WAY + *H.somnus* | 5.0 | 0.122 1.0X | 0.122 1.0X | 20/20 |
| 1093-3 | 6-WAY + *H.somnus* | 5.0 | 0.061 0.5 | 0.061 1.0X | 20/20 |
| 1093-4 | 6-WAY + *H.somnus* | 2.0 | 0.183 1.5X | 0.183 1.5X | 20/20 |
| 1093-5 | 6-WAY + *H.somnus* | 2.0 | 0.122 1.0X | 0.122 1.0X | 20/20 |

TABLE 3-continued

POTENCY TESTING OF THE PURIFIED *H. somnus* COMPONENT WHEN COMBINED WITH CLOSTRIDIAL COMPONENTS

| SERIAL NUMBER | TYPE OF PRODUCT | DOSE SIZE (mL) | AMOUNT OF *H. Somnus* PER DOSE* ISOLATE 8025T | AMOUNT OF *H. Somnus* PER DOSE* ISOLATE 14767 | POTENCY TEST RESULT (PROTECTED MICE/TOTAL INFECTED) |
|---|---|---|---|---|---|
| 1093-6 | 6-WAY + *H.somnus* | 2.0 | 0.061 0.5X | 0.061 0.5X | 19/20 |
| 1093-7 | 1093-5 DILUTED 1:2 | 2.0 | 0.5X | 0.5X | 19/20 |
| 1093-8 | 7-WAY + *H.somnus* | 2.0 | 0.061 1.0X | 0.061 1.0X | 20/20 |
| 1093-9 | 6-WAY + *H.somnus* | 2.0 | 0.244 1.5X | NONE | 20/20 |
| 1093-10 | 6-WAY + *H.somnus* | 2.0 | NONE | 0.244 1.0X | 18/20 |
| 1093-11 | *H.somnus* ONLY | 2.0 | 0.122 1.0X | 0.122 1.0X | 20/20 |

*The amount as designated by X indicates the concentration as relative to the original whole culture.

6-WAY components=*Cl. chauvoei, Cl. novyi, Cl. septicum,*
   Cl. sordellii, Cl. perfringenstypes C and D 7-WAY components=*Cl. chauvoei, Cl. novyi, Cl. septicum,*
   Cl. sordellii, Cl. perfringenstypes C and D,
   Cl. haemolyticum

*Cl. perfringens* type C contained 600 CPU per dose
*Cl. perfringens* type D contained 350 CPU per dose

Example 3

This example shows the effect of detrimental antigens on relatively weak protective antigen components such as *C. perfringes* types C and D. The effect of the detrimental antigens were evaluated in a multi-component vaccine containing protective antigen components from 6 clostridial organisms and one protective antigen component from one non-clostridial. Clostridial protective antigen components were produced as described in Example 1B. Serials were formulated with varying levels of *Cl. perfringens* type C and D toxoids. CPU levels for type C were adjusted to 600, 900, 1200 or 1800 per dose whereas CPU levels of type D toxoid were adjusted to 350, 500, 700 or 1000 per dose.

Six clostridial protective antigen components were combined with two protective antigen components from *H. somnus* in various formulations containing differing concentrations of the two *Cl. perfringens* protective antigen components. TABLE 4 illustrates the amounts of each protective antigen component added to the formulations excluding the *Cl. perfringens* types C and D.

TABLE 4

GENERAL PROTECTIVE ANTIGEN COMPONENT FORMULATIONS - PREADJUVANTED

| ORGANISM | MINIMUM AMOUNT OF COMPONENT/ DOSE | ACTUAL VOLUME OF COMPONENT/ DOSE | DESCRIPTION OF ANTIGEN |
|---|---|---|---|
| *Cl. chauvoei* | >0.2 mL of WC* | 0.2 mL | WC Nonconc. |
| *Cl. septicum* | 0.8 mL of WC* | 0.11 mL | WC 7.4X Concentrate |
| *Cl. novyi* | 2.0 CPU | 0.2 mL @ 10 CPU/mL | 2.0 CPU Toxoid + WC |
| *Cl. sordellii* | 27.0 CPU | 0.27 mL @ 100 CPU/mL | 27.0 CPU Toxoid + WC |
| *H. somnus* 8025T | Conc. equivalent to 1.0 mL of WC* at harvest | 0.122 mL | 10X Conc. Toxoid + WC |
| *H. somnus* 14767 | Conc. equivalent to 1.0 mL of WC* at harvest | 0.122 mL | 10X Conc. Washed cells |
| *Cl. haemolyticum* | 2.0 mL equivalents of whole culture | 0.28 mL | 7.2X Conc. Washed cells |

TABLE 4-continued

GENERAL PROTECTIVE ANTIGEN COMPONENT
FORMULATIONS - PREADJUVANTED

| ORGANISM | MINIMUM AMOUNT OF COMPONENT/ DOSE | ACTUAL VOLUME OF COMPONENT/ DOSE | DESCRIPTION OF ANTIGEN |
|---|---|---|---|
| Adjuvanted PBS | N/A | Amt. needed to bring total dose to 2.0 mL | N/A |

*WC = Whole Culture

Because *Cl. perfringens* types C and D were more purified toxoids in this experimental preparation, it was important to determine whether these protective antigen components would be adversely affected by the other clostridial protective antigen components or by a non-clostridial protective antigen component such as *H. somnus*. Therefore, this experiment involved preparation of a clostridial vaccine combined with *H. somnus* in a 2.0 mL dose size and included varying the amounts of the *Cl. perfringens* types C and D components. CPU levels of types C & D ranged from 600 to 1800 CPU per dose for type C and from 350 to 1000 CPU per dose for type D. TABLE 5 shows the *Cl. perfringens* types C & D components along with the test results after injection of animals.

The five multicomponent clostridial vaccines and one vaccine containing a plurality of clostridial protective antigen components combined with *H. somnus* were tested according to procedures required by the U.S. government Animal Plant Health Inspection Service (APHIS). Guinea pigs, rabbits or mice were used for the testing. For the clostridial components, guinea pigs or rabbits were vaccinated respectively with a dose equivalent to ⅕ or ½ the field dose. These animals were boostered 10 to 14 days later with the same dose of vaccine. Guinea pigs were challenged with live organisms of either *Cl. chauvoei* or *Cl. haemolyticum*. To correlate with protection in cattle, at least 80% of the guinea pigs must survive these challenges. Mice were vaccinated, boostered and challenged to demonstrate that a vaccine was protective against *H. somnus*. The challenge was a live culture of *H. somnus* which must kill at least 80% of the non-vaccinated control mice. An acceptable vaccine must protect 14 of 20 vaccinated mice. Rabbits were vaccinated, boostered and bled to test for antibody titers against *Cl. septicum, Cl. sordellii, Cl. novyi*, and *Cl. perfringens* types C and D. Antibody quantitation was conducted according to prescribed APHIS testing against known standard toxins and antitoxins.

Animal test results [comparing *Cl. perfringens* types C and D, *Cl. novyi* and *Cl. sordellii* antitoxin responses obtained with five multi-component vaccines containing protective antigen components from 7 clostridial organisms (7-way) and one multicomponent vaccine containing protective antigen components from 7 clostridial organisms and one Gram-negative organism (*H. somnus*)] indicate that as little as 600 CPU of *Cl. perfringens* type C and 350 CPU of *Cl. perfringens* type D are necessary to protect animals in a vaccine containing 7 clostridial protective antigen components. Three-fold increases in the amounts of these toxoids did not interfere with other protective antigen components of these multicomponent vaccines. When *H. somnus* was added to the 7 clostridial protective antigen components, there appeared to be a slight depression of response to the *Cl. perfringens* types C & D. Therefore, the amounts of these protective antigen components would be increased in order to assure host animal protection in a multicomponent vaccine containing at least one non-clostridial antigen. TABLE 5 (below) shows that CPU levels of 1200 for *Cl. perfringens* type C and 700 for *Cl. perfringens* type D compensate for the affect of *H. somnus*. Apparently, the amounts of *Cl. sordellii* and *Cl. novyi* can be decreased since the amounts thereof appear to be significantly greater than necessary to protect animals.

TABLE 5

CRITICAL POTENCY RESULTS OF 7-WAY AND 7-WAY + *H. somnus*

| | | ANTITOX UNITS* | | | |
|---|---|---|---|---|---|
| SERIAL | CL. PER-FRINGENS CPUs | Cl. perf. C | Cl. perf. D | Cl. novyi | Cl. sordellii |
| 3X1094-A 7-WAY | C = 600 CPU D = 350 CPU | >10.0 | 2.0 | 4–5 | >8 |
| 3X1094-B 7-WAY | C = 900 CPU D = 500 CPU | 10.0 | 2.0 | NT | NT |
| 3X1094-C 7-WAY | C = 1200 CPU D = 700 CPU | 20.0 | 3.0 | 3.0 | >8 |
| 3X1094-D 7-WAY | C = 1800 CPU D = 1000 CPU | 10.0 | 3.0 | NT | NT |
| 3X1094-E 7-WAY + *H. somnus* | C = 1200 CPU D = 700 CPU | 15.0 | 2.0 | 3.0 | 5–7 |
| 3X1094-F 7-WAY | C = 1200 CPU (pH adj. to 6.0) D = 700 CPU | 20.0 | 2.0 | NT | NT |

*Necessary for Host Animal Protection: *Cl. perf.* C = 10 au; *Cl. perf.* D = 2 au; *Cl. novyi* = 0.5 au; *Cl. sordellii* = 1.0 au
**NT = Not Tested Example 4

This example shows the incorporation of the protective antigen components from the clostridial organisms and *H. somnus* in a commercial size serial of a vaccine, and the test for potency of the components. A 160 L batch of 6-way clostridial product containing *Cl. chauvoei, Cl. septicum, Cl. novyi, Cl. sordellii, Cl. perfringens* types C and D was prepared in the proportions as listed in TABLE 4 and formulated as in Example 2 with *H. somnus* isolates 8025T and 14767 at a 1× concentration as described in Example 1A. This serial was tested for potency according to the previously-described APHIS requirements. The results of the tests are shown in TABLE 6. All protective antigen components of the 6-WAY clostridial plus *H. somnus* multicomponent vaccine showed potency results which exceed the minimum requirements for protection of animals as determined by APHIS.

TABLE 6

ANIMAL TEST RESULTS OF 6-WAY CLOSTRIDIAL + *H. somnus*

| ORGANISM | TEST ANIMAL TYPE OF TEST | REQUIREMENT FOR SATISFACTORY POTENCY | POTENCY RESULT (live/total) |
|---|---|---|---|
| Cl. chauvoei | Guinea Pig Challenge | 7/8 guinea pigs must survive challenge | 8/8 |
| Cl. septicum | Rabbit Challenge | 7/8 rabbits must survive challenge | 8/8 |
| Cl. novyi | Rabbit Serology | 0.5 antitoxin units in the rabbit serum | 4.0 au |
| Cl. sordellii | Rabbit Serology | 1.0 antitoxin units in the rabbit serum | >10.0 au |
| Cl. perfringens Type C | Rabbit Serology | 10.0 antitoxin units in the rabbit serum | 25.0 au |
| Cl. perfringens Type D | Rabbit Serology | 2.0 antitoxin units in the rabbit serum | 3.0 au |
| H. somnus | Mouse Challenge | 15 of 20 mice must survive the challenge | 20/20 |

Example 5

Seven clostridial protective antigen components were combined with the protective antigen component from *H. somnus* according to the procedures described in Example 2 and tested in APHIS-required potency tests (as described previously) as a 2.0 mL dose. The actual formulation specifications are listed in TABLE 7. Results of the APHIS-required animal testing are shown in TABLE 8. All the protective antigen components passed the testing. These data demonstrate that 7 clostridial protective antigen components can be combined with a protective antigen component from *H. somnus* or some other non-clostridial organism to produce a vaccine which is immunogenically effective. In fact, there is little difference between the animal test results produced by the 6-way plus *H. somnus* and those produced by the 7-way plus *H. somnus* (compare results in TABLES 6 and 8).

TABLE 7

FORMULATION OF PROTECTIVE ANTIGEN COMPONENTS OF 7-WAY + *H. somnus* SERIAL 102994

| ORGANISM | STRAIN | LOT NUMBER | CONC. | AMOUNT PER 2.0 mL DOSE |
|---|---|---|---|---|
| Cl. chauvoei | 5677-2 | 264 | NONE | 0.400 mL |
| Cl. septicum | 6750-2 | 296 | 6.6X | 0.121 mL |
| Cl. novyi | 3047 | 165 | NONE | 0.167 mL |
| Cl. sordellii | 4513 | 227 | NONE | 0.090 mL |
| Cl. haemolyticum | 5982 | 194 | 7.15X | 0.280 mL |
| Cl. perfringens type C/B | 3602 | 540 | NONE | 0.400 mL |
| Cl. perfringens type D/B | 455E | 155 | NONE | 0.364 mL |
| H. somnus | 8025T | N/A | 20X | 0.061 mL |

TABLE 7-continued

FORMULATION OF PROTECTIVE ANTIGEN COMPONENTS OF 7-WAY + *H. somnus* SERIAL 102994

| ORGANISM | STRAIN | LOT NUMBER | CONC. | AMOUNT PER 2.0 mL DOSE |
|---|---|---|---|---|
| H. somnus | 14767 | N/A | 20X | 0.061 mL |
| Adjuvanted PBS | N/A | N/A | N/A | 0.056 mL |

TABLE 8

ANIMAL TEST RESULTS PRODUCED BY 7-WAY + *H. somnus*

| ORGANISM | TEST ANIMAL TYPE OF TEST | REQUIREMENT FOR SATISFACTORY POTENCY | POTENCY RESULT 7-WAY + *H. somnus* |
|---|---|---|---|
| Cl. chauvoei | Guinea Pig Challenge | 7/8 guinea pigs must survive challenge | 8/8 Live/Total |
| Cl. septicum | Rabbit Challenge | 7/8 rabbits must survive challenge | 8/8 Live/Total |
| Cl. novyi | Rabbit Serology | 0.5 antitoxin units in the rabbit serum | >0.5 Antitoxin Units |
| Cl. sordellii | Rabbit Serology | 1.0 antitoxin units in the rabbit serum | >1.0 Antitoxin Units |
| Cl. perfringens Type C | Rabbit Serology | 10.0 antitoxin units in the rabbits serum | >10.0 Antitoxin Units |
| Cl. perfringens Type D | Rabbit Serology | 2.0 antitoxin units in the rabbit serum | >2.0 Antitoxin Units |
| Cl. haemolyticum | Guinea Pig Challenge | 7/8 guinea pigs must survive challenge | 8/8 Live/Total |
| H. somnus | Mouse Challenge | 14 of 20 mice must survive challenge | 16/20 Live/Total |

Example 6

This example illustrates vaccines wherein viruses are combined with clostridial components. Modified live infectious bovine rhinotracheitis virus (IBRV) was combined with a plurality of clostridial protective antigen components (*Cl. perfringens* types C and D).

The clostridial protective antigen components were prepared and formulated according to methods discussed in Example 1B. The IBRV utilized for this experiment was one which had been modified such that it would not cause a disease if the live virus is injected into animals. Vaccines prepared from such viruses are called modified live vaccines. Since modified live vaccines contain live viruses as their protective antigen component, the efficacy of such vaccines depends on the amount of live virus contained within them. It has been determined by cattle vaccination/challenge studies that infectious bovine rhinotracheitis virus when prepared in a lyophilized vaccine protects cattle if the titer is at least $10^{4.2}TCID_{50}/mL$. The reference IBRV used for this experiment was grown in roller bottle culture on bovine kidney cells after which the IBRV harvest fluids were lyophilized such that the titer post lyophilization was $10^{7.0}/mL$.

To avoid loss of efficacy of the vaccine, the multicomponent vaccine containing protective antigen components from Cl. perfringens types C and D and from IBRV are formulated as a two-container vaccine. One container will contain the lyophilized modified live IBRV protective antigen component and the second container will contain the inactivated, adjuvanted liquid Cl. perfringens types C and D protective antigen components. In using the vaccine, the liquid Cl. perfringens types C and D protective antigen component is removed from its container with a syringe and injected into the lyophilized modified live IBRV container causing rehydration of the lyophilized IBRV. In order to determine whether a modified live virus is negatively affected by the rehydration, one retitrates the combined multicomponent vaccine. If there is a detrimental effect (viricidal activity) of the rehydration of the virus protective antigen component it will be apparent within the first 2 hours after rehydration. Therefore, all such modified live vaccines which are combined with non-modified live components should be tested for and pass a virucidal activity test. APHIS defines viricidal activity as the loss of more than 0.7 logs of virus titer within 2 hours after rehydrating the virus component. Any multicomponent vaccine in which the virus protective antigen component loses more than 0.7 logs of virus titer within 2 hours post rehydration by the diluent therefore would be considered to have failed the viricidal activity test.

Several formulations of the 3-way multicomponent vaccine containing Cl. perfringens types C and D and IBRV were prepared and formulated. An APHIS-required viricidal activity test was conducted on each of these formulations. The specifics of the formulation of the combinations and results of the viricidal activity testing are shown in TABLE 9. It is apparent that all formulations, even those containing non-purified Cl. perfringens types C and D were acceptable showing no viricidal activity. Therefore, it has been demonstrated that a plurality of clostridial protective antigen components can be added to virus protective antigen components without causing a detrimental effect when prepared according to the methods described herein. More specifically there were no contrary indications that clostridial protective antigen components or adjuvants or combinations thereof are virucidal, or that there was an interference between the clostridial protective antigen components and the virus protective antigen components.

TABLE 9

FORMULATION AND TESTING OF COMBINATION Cl. perfringens types C and D + IBRV

| SERIAL NO. TESTED AS | Cl. perfringens Type C | | Cl. perfringens Type C | | IBRV TITER | IBRV (LOG CHANGE |
|---|---|---|---|---|---|---|
| A 20. mL DOSE | Amount of Purif. | CPU | Amount of Purif. | CPU | POST REHYD. | IN TITER) |
| 12X894-A | NON-PURIF. CELL-FREE TOXOID | 600 | NON-PURIF. CELL-FREE TOXOID | 400 | $10^{7.5}$ | +0.5 |
| 12x894-B | NON-PURIF. CELL-FREE TOXOID | 1200 | NON-PURIF. CELL-FREE TOXOID | 700 | $10^{7.0}$ | 0.0 |
| 12X894-C | PURIF. CELL-FREE TOXOID | 600 | PURIF. CELL-FREE TOXOID | 400 | $10^{7.0}$ | 0.0 |
| 12X894-D | PURIF. CELL-FREE TOXOID | 900 | PURIF. CELL-FREE TOXOID | 550 | $10^{6.9}$ | −0.1 |
| 12X894-E | PURIF. CELL-FREE TOXOID | 1200 | PRUIF. CELL-FREE TOXOID | 700 | $10^{6.7}$ | −0.3 |

NOTE: The reference titer for the IBRV rehydrated with sterile diluent was $10^{7.0}$.

The Cl. perfringens types C and D from the above multicomponent vaccines were also tested for potency in order to assure that the virus did not have a detrimental effect on the clostridial protective antigen components. Results of the clostridial testing are shown in TABLE 10. It was found that the clostridial protective antigen components were not detrimentally affected by the virus component. Apparently, the purification improved the potency of the clostridial protective antigen components, as does addition of antigen. This was evidenced by higher CPUs producing higher rabbit antitoxin units. This example shows that clostridial protective antigen components and virus protective antigen components can be successfully combined to produce effective multicomponent vaccines.

TABLE 10

POTENCY RESULTS OF THE Cl. Perfringens types C and D FROM THE COMBINATION CLOSTRIDIAL VACCINE CONTAINING IBRV

| | | Cl. | | Rabbit Units Antitox | |
|---|---|---|---|---|---|
| SERIAL NO. | DESCRIPTION | Cl. perf. Type C CPU | Cl. perf. Type D CPU | Cl. perf. type C | Cl. perf. type D |
| 12X894-A | NON-PURIFIED CELL-FREE TOXOID | 600 | 400 | 20–30 | 3–4 |
| 12X894-B | NON-PURIFIED CELL-FREE TOXOID | 1200 | 700 | 20–30 | 4–5 |
| 12X894-C | PURIFIED CELL-FREE TOXOID | 600 | 400 | 30–40 | >5 |
| 12X894-D | PURIFIED CELL-FREE TOXOID | 900 | 550 | 40–60 | 5–6 |
| 12X894-E | PURIFIED CELL-FREE TOXOID | 1200 | 700 | 30–40 | >6 |

Example 7

This example shows that a larger combination of virus protective antigen components and clostridial protective antigen components could be successfully prepared in a low dose formulation. Several preparations of Cl. perfringens types C and D protective antigen components were prepared as described in Example 1B and combined with modified live IBRV, modified live bovine virus diarrhea virus (BVDV), modified live parainfluenza type 3 virus (PI$_3$) and modified live bovine respiratory syncytial virus (BRSV). The four modified live virus protective antigen components were prepared by art-known techniques. As part of the preparation, the detrimental effect of the clostridial protective antigen components on any of the modified live virus protective antigen components was determined. Therefore, the APHIS-required viricidal activity test was conducted on the various multicomponent vaccines. Since clostridial vaccines historically contain residual formaldehyde as a preservative and since it is known that formaldehyde can have a detrimental effect on modified live viruses, part of this experiment involved adding known amounts of formaldehyde to the formulations to determine maximum allowable amounts of this preservative. TABLE 11 lists the formulation differences and the results of the viricidal activity testing for the four virus protective antigen components. The results indicate that the clostridial protective antigen components are somewhat viricidal especially to IBRV and BVDV. Additionally, higher concentrations of formaldehyde significantly reduce the titers of these two virus whereas BRSV and PI$_3$V are only adversely affected by the highest level of formaldehyde. However, it is apparent that such a combination of clostridial protective antigen components and modified live virus protective antigen components would be commercially viable. This experiment also demonstrates that purification of the clostridial protective antigen components may not be required.

TABLE 11

RESULTS OF THE VIRICIDAL ACTIVITY TESTING FOR THE COMBINATION CONTAINING MULTIPLE CLOSTRIDIAL AND VIRAL PROTECTIVE ANTIGEN COMPONENTS

| SERIAL | DE-SCRIPTION | IBRV TITER/ LOG CHANGE IN TITER | BVDV TITER/ LOG CHANGE IN TITER | PI$_3$ TITER/ LOG CHANGE IN TITER | BRSV TITER/ LOG CHANGE IN TITER |
|---|---|---|---|---|---|
| 4X1594-A | NON-PURIF. Cl. perfringens types C and D, 0.1% Form. | $10^{7.6}$ −0.1* | $10^{6.6}$ −0.8 | $10^{7.0}$ −0.3* | $10^{5.9}$ −0.0* |
| 4x1594-B | NON-PURIF. Cl. perfringens types C and D, 0.1% Form. | $10^{7.1}$ −0.6* | $10^{6.9}$ −0.5* | $10^{7.3}$ −0.0* | $10^{5.8}$ −0.1* |
| 4X1594-C | NON-PURIF. Cl. perfringens types C and D, 0.17% Form. | $10^{6.9}$ −0.8 | $10^{6.0}$ −1.4 | $10^{6.9}$ −0.4* | $10^{5.7}$ −0.2* |
| 4X1594-D | NON-PURIF. Cl. perfringens types C and D, 0.25% Form. | $10^{6.6}$ −1.1 | $10^{5.7}$ −1.7 | $10^{6.9}$ −0.4* | $10^{5.7}$ −0.2* |
| 4X1594-E | NON-PURIF. | $10^{6.0}$ −1.7 | $10^{5.9}$ −1.5 | $10^{6.3}$ −1.0 | $10^{5.2}$ −0.7* |
| 4X1594-F | Cl. perfringens types C and D, 0.32% Form. NON-PURIF. CELL-FREE Cl. perfringens types C and D, 0.05% Form. | $10^{7.0}$ −0.7* | $10^{6.8}$ −0.6* | $10^{7.5}$ +0.2* | $10^{5.7}$ −0.2* |

Reference Virus titers $10^{7.7}$ $10^{7.4}$ $10^{7.3}$ $10^{5.9}$
FORM. = Formaldehyde Example 8

This example illustrates the safety of the vaccines of the invention. In order to show that the described low dose, multicomponent vaccines are actually safer for animals and would not cause significant animal reactivity, including injection site lesions (as routinely noted with the current 5.0 mL dose clostridial combination products on the market) several field safety studies were conducted. The first study involved a comparison of injection sites from cattle injected subcutaneously with either a 5.0 mL dose, 6-way conventional clostridial product or a 2.0 mL dose multicomponent vaccine comprising protective antigen components from 6 clostridial organisms (6-way clostridial vaccine) prepared according to the methods described herein.

Two sources of yearling cattle were randomly allocated to treatment groups of 54 head each. Two-milliliter dose 6-way clostridial vaccine (formulated as in Example 2) was given subcutaneously to one group and 5.0 mL dose, 6-way vaccines formulated via conventional methods but containing the modified carbopol adjuvant was administered subcutaneously to the other group. The cattle were commingled throughout the trial. Evaluations of the injection sites were made on days 7, 21, 49 and 95 days post injection. Results are shown in FIGS. 1 and 2. On day 7, all animals had a palpable injection site response in both groups. The animals receiving the 2.0 mL dose multicomponent vaccine had significantly smaller lesions than the animals receiving the 5.0 mL dose conventional product (p=<0.0001). This difference continued on days 21, 49 and 95. At slaughter (95 days) there were significantly fewer (p=<0.001) 2.0 mL dose vaccinates with lesions (3.5%) as compared to the 5.0 mL dose vaccinates with lesions (30%). Additionally, the 2.0 mL dose vaccinates had consistently smaller lesions at the injection sites.

In the second field safety study, calves with a known injection history were used to evaluate the incidence and duration of injection site lesions in carcasses from animals injected intramuscularly. The calves were at branding and weaning age. Forty-two steer calves and 42 heifer calves, of known history, located at Colorado State University, were selected for the study. These calves had received no injections prior to the beginning of the trial and were individually identified using plastic ear tags and assigned randomly to a product treatment group. A 5.0 mL dose conventional 6-way clostridial product or a 2.0 mL dose 6-way clostridial multicomponent vaccine prepared by the methods of this invention were administered in the semimembranosus muscle (inside round steak location) at branding using an 18 gauge, 1-inch needle. Animals were vaccinated with the same vaccines at weaning. However, injections were administered in the biceps femoris (top and gluteus medium muscles (top sirloin butt location) using a 16 gauge, 1.5 inch needle. Calves were managed from birth to slaughter. Following weaning, animals were fed a typical finishing diet. Calves were branded at approximately 1.5 months of age, weaned at 6.5 months of age and slaughtered at 14 months of age. At slaughter, 82.7% of the cattle graded choice or better. Upon completion of the finishing phase, steers were slaughtered/dressed using conventional procedures. Following the slaughter process, the top sirloin butt and inside round subprimal cuts were collected. From a total of 84 head, 160 inside rounds and 159 top sirloin butts were collected after slaughter and fabrication at the packing plant. Cuts were subjected to evaluation, dissection into one-inch strips and observation for the presence of injection-site lesions. Results showing the incidence of lesions, the distribution of lesions by score and the quantity of trim required to remove the lesions are presented in TABLES 12,13 and 14.

TABLE 12

INCIDENCE OF INJECTION-SITE LESIONS AFTER INJECTING 5.0 mL DOSE OR 2.0 mL DOSE 6-WAY CLOSTRIDIAL VACCINES

| 6-WAY VACCINE DOSE | INCIDENCE OF LESIONS | | | |
|---|---|---|---|---|
| | NUMBER | BRANDING | NUMBER | WEANING |
| 5.0 mL | 38 OF 41 | 92.7% | 31 OF 39 | 79.5% |
| 2.0 mL | 29 OF 40 | 72.5% | 19 OF 41 | 46.3% |

TABLE 13

LESION CLASSIFICATION BY INJECTION TIME AND VACCINE INJECTED

| TYPE OF LESION | 5.0 mL 6-WAY VACC. AT BRANDING | Dose Clostridial VACC. AT WEANING | 2.0 mL 6-WAY VACC. AT BRANDING | Dose Clostridial VACC. AT WEANING |
|---|---|---|---|---|
| CALLOUSED LESION | 33 | 27 | 22 | 19 |
| CLEAR LESION | 5 | 4 | 7 | 0 |
| MINERAL-IZED LESION | 0 | 0 | 0 | 0 |
| LESION WITH NODULES | 0 | 0 | 0 | 0 |
| LESIONS WITH FLUID | 0 | 0 | 0 | 0 |

VACC = VACCINATION

TABLE 14

QUANTITY OF TRIM (IN GRAMS) TO REMOVE INJECTION SITE LESIONS AFTER INJECTING 5.0 mL DOSE OR 2.0 mL DOSE 6-WAY CLOSTRIDIAL VACCINES INTRAMUSCULARLY INTO CALVES AT BRANDING OR WEANING

| | QUANTITY OF TRIM TO REMOVE LESION | | | |
|---|---|---|---|---|
| 6-WAY VACCINE DOSE | NUMBER OF CALVES | LESIONS WHEN VACC. AT BRANDING | NUMBER OF CALVES | LESIONS WHEN VACC. AT WEANING |
| 5.0 mL Conventional | 38 | 86.0 | 31 | 69.4 |
| 2.0 mL | 29 | 48.8 | 19 | 30.3 |

These results indicate that a 2.0 mL dose 6-way multicomponent clostridial vaccine of the invention was less reactive in calves than a 5.0 mL dose conventional technology 6-way clostridial product. The incidence of lesions was significantly lower (p=<0.05) for the 2.0 mL group than for the 5.0 mL group when administration occurred at both branding and weaning times. The blemishes resulting from use of the 5.0 mL clostridial also necessitated more trim (p=<0.05) to remove the lesions than was the case for those in the 2.0 mL group.

In the final field safety trial, a 2.0 mL dose vaccine containing 6 clostridial protective antigen components combined with protective antigen components from $H.$ $somnus$ was prepared according to the methods described in Example 2 and administered to 1,528 calves by six veterinarians in five states. The field trial was conducted from November 1994 through January 1995. Vaccine was administered by the normal routes of administration for the herd and included both intramuscular and subcutaneous routes. Veterinarians were requested to observe the calves for injection site reactions and/or lesions. At the end of the trial, no significant unfavorable local or systemic reactions were noted by any of the participating veterinarians.

As a result of these field safety studies, especially the final study which involved a true field evaluation of a commercial-size production serial, it has been demonstrated that a multicomponent vaccine containing protective antigen components from at least 6 clostridial organisms, protective antigen components from at least one non-clostridial organism such as a Gram-negative bacteria like $H.$ $somnus$ and an adjuvant such as carbopol, can be produced commercially in a dose volume less than 3.0 mL and safely injected to protect animal under field conditions.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A multicomponent vaccine for cattle, comprising:
   an immunogenically effective combination of a protective antigen component from at least 6 clostridial organisms,
   a protective antigen component from a non-clostridial organism, which is
   *Hemophilus somnus*, and
   further comprising an adjuvant wherein the vaccine is in a low dose volume of about 2.0 mL or less.

2. The vaccine according to claim 1, wherein the clostridial organisms are selected from the group consisting of *Clostridium chauvoei, Clostridium septicum, Clostridium novyi, Clostridium perfringens* type C, *Clostridium perfringens* type D, *Clostridium sordellii, Clostridium haemolyticum* and *Clostridium tetani*.

3. The vaccine according to claim 1, wherein the adjuvant is selected from the group consisting of a polymer, a block co-polymer, an oil-in-water emulsion, a water-in-oil emulsion, $Al(OH)_3$, $AlPO_4$, an extract of a bacterial cell wall, an extract of a plant cell wall, a liposome, and a saponin.

4. The vaccine according to claim 1, wherein the 6 clostridial organisms are selected from the group consisting of *Cl. chauvoei, Cl. septicum, Cl. novyi, Cl. perfringens* type C, *Cl. perfringens* type D, *Cl. haemolyticum* and *Cl. sordellii*.

5. The vaccine according to claim 1, wherein a protective antigen component is obtained from 7 clostridial organisms.

6. The vaccine according to claim 5, wherein the 7 clostridial organisms are selected from the group consisting of *Cl. chauvoei, Cl. septicum, Cl novyi, Cl. perfringens* type C, *Cl. perfringens* type D, *Cl. sordellii, Cl. haemolyticum*, and *Cl. tetani*.

7. A multicomponent vaccine for cattle, comprising:
a safe and immunogenically effective combination of a protective antigen component from 6 clostridial organisms which are *Cl. chauvoei, Cl. septicum, Cl novyi, Cl. perfringens* type C, *Cl. perfringens* type D, and *Cl. sordellii;*
a protective antigen component from a non-clostridial organism, which, is *H. somnus* and
an adjuvant, wherein the vaccine is in a low dose volume of about 2.0 mL or less.

8. A multicomponent vaccine for cattle, comprising:
a safe and immunogenically effective combination of a protective antigen component from 7 clostridial organisms which are *Cl. chauvoei, Cl. septicum, Cl novyi, Cl. perfringens* type C, *Cl. perfringens* type D, *Cl. haemolyticum* and *Cl. sordellii;*
a protective antigen component from a non-clostridial organism, which is *H. somnus*, and
an adjuvant, wherein the vaccine is in a low dose volume of about 2.0 mL or less.

9. A method of administering the vaccine of claim 1 to cattle, comprising:
intramuscularly or subcutaneously vaccinating the cattle.

* * * * *